(12) United States Patent
Osborne et al.

(10) Patent No.: US 10,085,878 B2
(45) Date of Patent: Oct. 2, 2018

(54) CONDOM CONTAINER AND APPLICATOR

(75) Inventors: Patrick H. Osborne, Ft. Lauderdale, FL (US); Russell B. Boy, Ft. Lauderdale, FL (US)

(73) Assignee: Peak A Holdings, LLC, Ft. Lauderdale, FL (US)

( * ) Notice: Subject to any disclaimer, the term of this patent is extended or adjusted under 35 U.S.C. 154(b) by 229 days.

(21) Appl. No.: 13/484,416

(22) Filed: May 31, 2012

(65) Prior Publication Data

US 2013/0319425 A1    Dec. 5, 2013

(51) Int. Cl.
*A61F 6/04* (2006.01)
*A61F 6/00* (2006.01)

(52) U.S. Cl.
CPC ................... *A61F 6/005* (2013.01)

(58) Field of Classification Search
CPC ................. A61F 6/04; A61F 6/005
USPC .......... 128/842, 844, 918, 830; 206/69, 278, 206/281, 524.8, 813; 604/346, 347, 349, 604/351, 352; 221/45, 59, 226, 232, 268, 221/271, 279, 282; 312/35, 42
See application file for complete search history.

(56) References Cited

U.S. PATENT DOCUMENTS

| | | | | | |
|---|---|---|---|---|---|
| 4,281,648 | A | * | 8/1981 | Rogers | A61F 6/04 128/844 |
| 4,961,734 | A | * | 10/1990 | Kassman | A61F 6/005 128/844 |
| 5,038,969 | A | * | 8/1991 | Berger | 221/40 |
| 5,205,298 | A | * | 4/1993 | Hurst | A61F 6/00 128/842 |
| 5,437,286 | A | | 8/1995 | Stratton | |
| 5,549,196 | A | * | 8/1996 | Kassman | 206/69 |
| 5,713,488 | A | * | 2/1998 | Farrugia | A61F 6/005 221/226 |
| 2010/0206752 | A1 | * | 8/2010 | Nikitczuk | A61F 6/005 206/69 |
| 2010/0252051 | A1 | * | 10/2010 | Morgan | A61F 6/005 128/844 |

OTHER PUBLICATIONS

International Search Report issued in connection with PCT/US2013/043590.
Written Opinion issued in connection with PCT/US2013/043590.

* cited by examiner

*Primary Examiner* — Ophelia A Hawthorne
*Assistant Examiner* — Caitlin Carreiro
(74) *Attorney, Agent, or Firm* — Akerman LLP (57) ABSTRACT

A condom, container and applicator for a condom, in which the condom is provided in a longitudinally expandable cup having a peel-off lid. The cup is typically formed of plastic material. The side wall of the container is expandable, and can include accordion-like pleats to allow for longitudinal expansion of the cup. The condom is placed in the cup such that it can be directly applied to the penis while still in the cup, and the cup used as an applicator to unroll the condom over at least the head of the penis by expanding the side wall of the cup. The disclosure also relates to a dispenser for storing and dispensing the condom containers.

17 Claims, 6 Drawing Sheets

CONDOM CONTAINER AND APPLICATOR

FIELD OF THE INVENTION

This disclosure relates generally to packaging for condoms that functions as both a container and applicator.

BACKGROUND OF THE INVENTION

Condoms are typically packaged in individually sealed packaging, that the user tears open. Typically, the packaging is formed of two sheets of foil that are heat-sealed together to form a generally square pocket that is designed to be accessed by tearing through the heat-sealed edges. Once the packaging has been torn open, it can be difficult to tell which is the correct side of the rolled-up condom that should be placed against the head of the penis in order for the condom to be unrolled easily, especially in the dark. The tear-open packaging can also not be re-used for sanitary disposal of the used condom. Additionally, the tear-open packaging is not easy to store neatly, and does not present any visual appeal.

SUMMARY OF THE INVENTION

The present disclosure relates to a container and applicator for a condom that is provided with the condom supplied therein. The container includes a longitudinally expandable cup or base, and a peel-off lid. The cup is typically formed of plastic material. The side wall of the container is expandable, and can include accordion-like pleats to allow for longitudinal expansion of the cup. The condom is placed in the cup such that it can be directly applied to the penis while still in the cup, and the cup used as an applicator to unroll the condom over at least the head of the penis by expanding the side wall of the cup.

The container and applicator allows for quick opening thereof, and allows the condom to be quickly and easily applied to the penis without the user having to figure out which is the correct side of the condom that will allow for easy unrolling thereof In addition, the user does not have to touch the inside of the condom during the application process. In some arrangements, the container can expand to allow the condom to be entirely unrolled onto the penis without the user needing to touch the condom, and in other arrangements, the container expands enough to place the condom over the head of the penis so that the user can unroll it the rest of the way over the shaft.

The present disclosure also relates to a condom dispenser including a dispenser body with at least two condom containers removably provided in the dispenser body. The condom containers include a base having a longitudinally expandable side wall, a closed end wall and an open end, the base having a generally circular cross section, and a peel away lid attached to the open end of the base. A condom is provided in the base of each condom container such that the condom may be directly applied to the penis while still in the base and may be rolled onto the penis by expanding the height of the base.

The dispenser body can include a cartridge having an open end and a spring biased platform, the condom containers being placed within the cartridge on the spring biased platform such that the condom containers are biased towards the open end of the dispenser body. A removable dispenser can be included that can be detached from the dispenser body, the removable dispenser allowing a user to carry at least two condom containers separately from the dispenser body.

The present disclosure further relates to a condom dispenser including a dispenser body, a cartridge for receiving a plurality of condom containers, and having an opening for dispensing a condom container therefrom, and a spring-biased arm attached to the dispenser body, the spring-biased arm acting against a wall of a condom container to urge the condom container into a dispensing position in the opening of the cartridge. The condom container is adapted to have at least one rigid side wall against which the spring-biased arm can act.

The dispensing opening can be an open end of the cartridge, and the dispenser body can include a spring biased platform for receiving the condom containers such that the condom containers are biased towards the open end of the dispenser body. Alternatively, the cartridge can include an open end for receiving a plurality of condom containers, and a dispensing opening positioned at a lower end of the dispensing body.

BRIEF DESCRIPTION OF THE DRAWINGS

Further objectives and advantages of the invention can become more apparent from the following description and claims and from the accompanying drawings herein.

DETAILED DESCRIPTION OF THE EMBODIMENTS OF THE INVENTION

Figure 1:
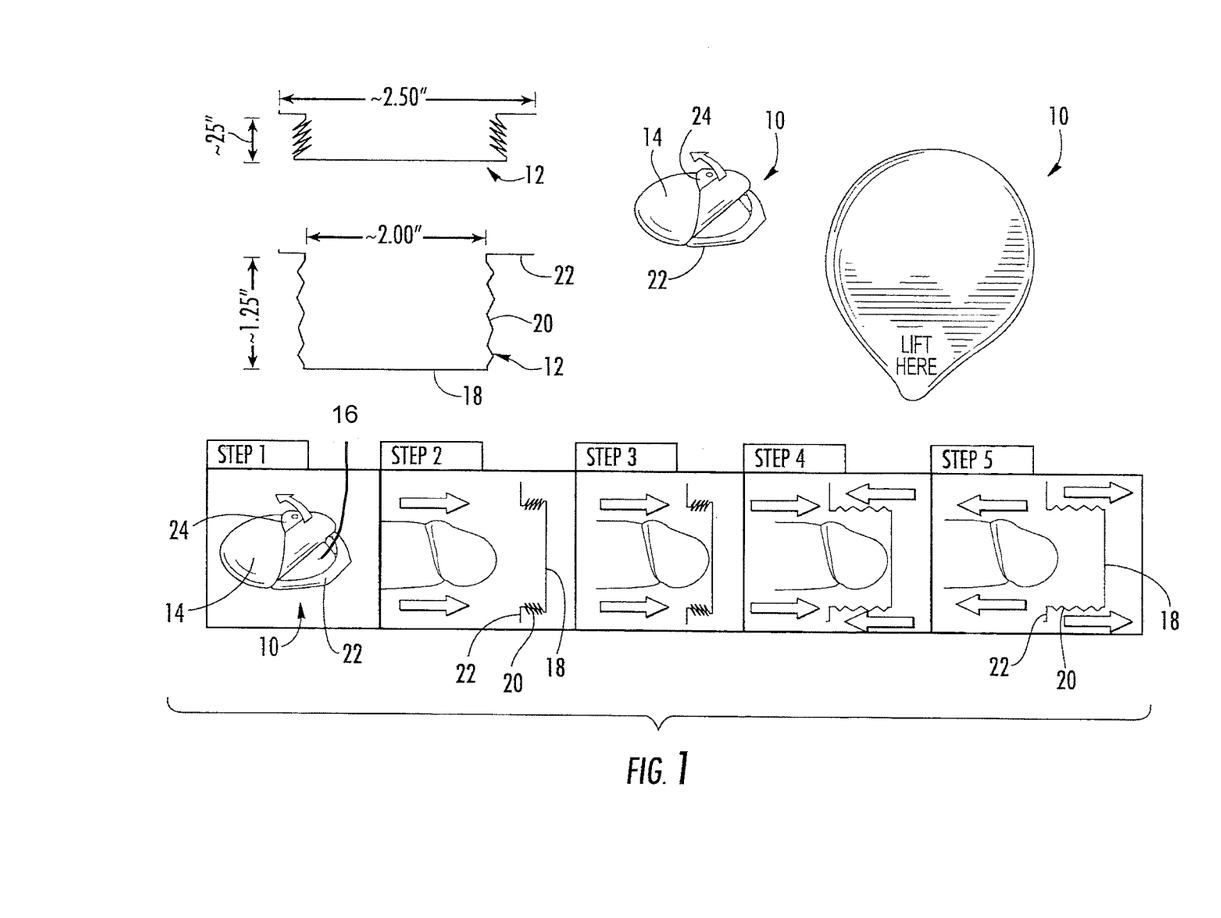
FIG. 1 shows a side schematic view of a condom container, and a schematic showing use of the container as an applicator.
Figure 2:
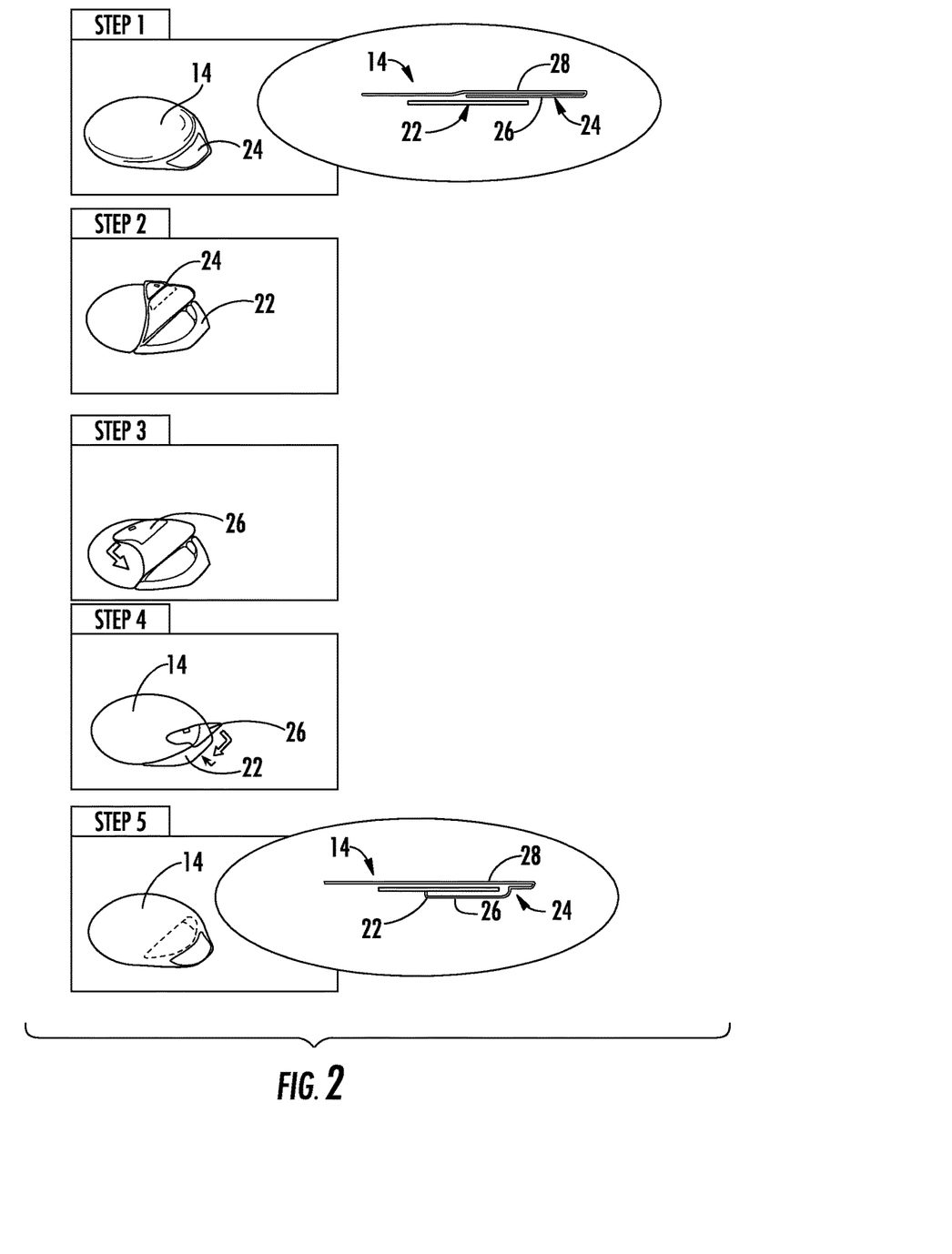
FIG. 2 shows schematic views of the resealable top of the container.
Figure 3:
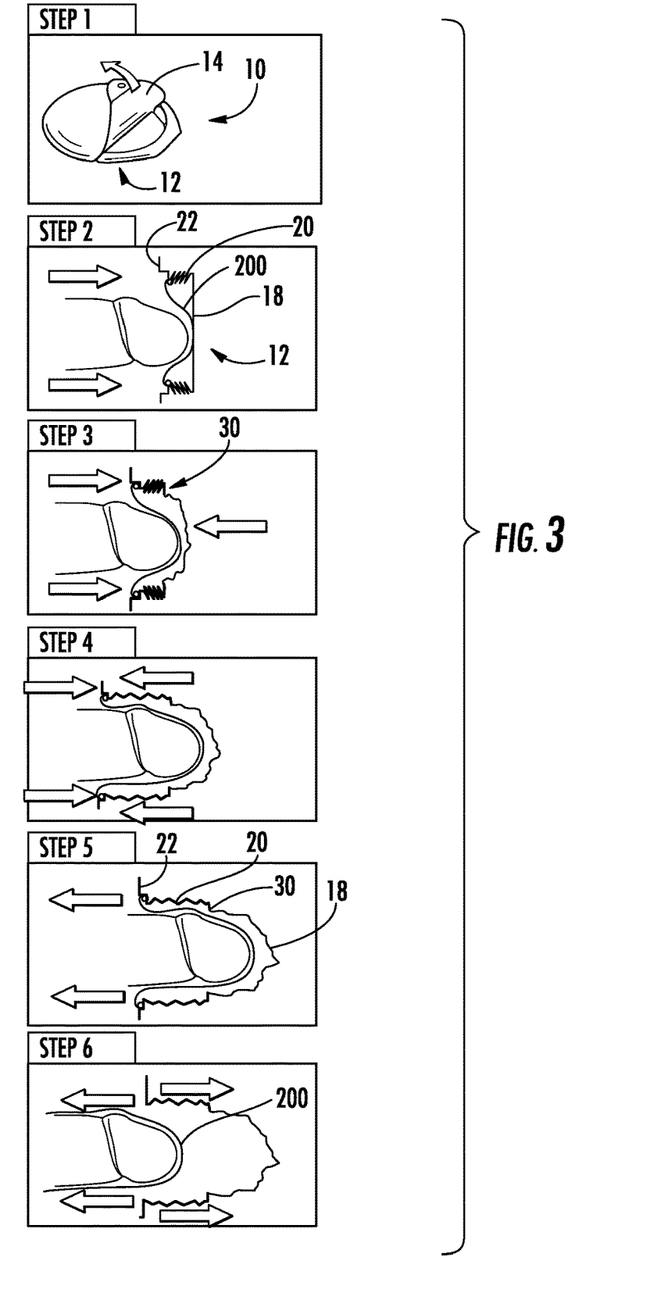
FIG. 3 shows a schematic of use of an alternative arrangement of the container.

With reference to FIGS. 1-3, a condom container 10 is illustrated. The container 10 comprises an expandable base 12 that is generally in the form of a cup and a resealable lid 14, which will be described in more detail in the following.

The expandable base 12 is formed from any suitable material, and is preferably a plastic material that is rigid enough to retain its shape while still being somewhat thin and flexible. Other suitable materials include rubber, latex, and the like. In a preferred arrangement, the base 12 has a substantially cylindrical shape, with one open end 16 and a closed base end 18. A side wall 20 extends between the open end 16 and the closed base end 18. Thus, the base generally forms a cup for receiving a condom. The side wall 20 is longitudinally expandable so that the height or length of the base 12 can be increased, and in one arrangement the side wall 20 may be folded into an accordion-like or pleated arrangement to allow for such expansion. In other arrangements, the side wall 20 may be expandable in other ways, such as by unrolling, or by using a stretchable material to form the wall 20. A lip or flange 22 may be provided on the open end 16. In one arrangement, the external diameter of the lip 22 may be approximately 2.5", and the internal diameter of the base 12 may be approximately 2.0". It will of course be appreciated that different sizes of containers may be provided, to suit different condom sizes. The base 12 may have a depth of approximately 0.25" to approximately 0.3875" in an unexpanded configuration, and may have a depth of approximately 1.25" in an expanded configuration. It will be appreciated that the depth of the base 12 in the expanded configuration may be significantly larger in some arrangements.

The lid 14 is preferably formed of a flexible foil or plastic material. The lid 14 can be sealed to the base 12 with an adhesive (not shown), to provide a generally air-tight seal. The adhesive may be of any suitable type, but is preferably one that allows a user to peel the lid 14 from the base 12 relatively easily, such as is known from existing food packaging. The lid 14 can include a generally triangular latch tab 24 including relatively rigid plastic that the user can use to grasp the lid 14 in order to peel it back from the base 12.

A condom is provided in the container 10 in the typical rolled up configuration. The condom can either be provided loose in the container 10, or the rolled edge of the condom can be placed onto the lip 22, with the container sized to have a slightly smaller diameter than the typical diameter of the rolled edge of the condom. In any arrangement, the condom is supplied with the correct side facing the top of the container 10 so that the condom can be easily unrolled. That is, the rolled edge of the condom faces away from the lid 14.

The container 10 can be used as an applicator to help the user to quickly and easily apply the condom on the penis. As the condom is provided in the container with the correct side for unrolling facing towards the lid 14, once the lid is removed or peeled back, the container 10 is directly applied to the penis, meaning that the condom does not need to be removed from the container before application. The container 10 can then be expanded to assist in unrolling the condom onto the penis. This allows a condom to be easily applied in the dark, during peak anticipation, without the user having to figure out which way the condom is rolled up or potentially dropping the condom. In particular, either with the rolled edge of the condom pre-supplied on the lip 22, or with the rolled edge of the condom placed onto the lip 22 by the user, the user can push container 10 onto the penis by grasping the container just beneath the lip 22, which allows the lip 22 to push on the rolled edge of the condom, thereby unrolling it. Alternatively, the user can grasp the side wall 20 of the container 10 either close to the closed base end 10 or just behind the rolled edge of the condom, and can use the side wall 20 to push on the rolled edge of the condom. The container 10 does not need to expand all the way down the shaft of the penis, as once the condom is initially applied past the head of the penis, the user can remove the container 10, and continue unrolling the condom in the usual way.

FIG. 2 shows an arrangement of the lid 14 that can be reclosed for sanitary disposal of the used condom. The latch tab 24 includes two layers of relatively rigid plastic that are sealed together at only an outer edge portion of the tab. The two layers of the tab are sealed together such that a lower layer 26 of the tab 24 can be partially separated from an upper layer 28 by curling the foil lid 14 backwards. In this arrangement, the lip 22 of the container 10 may be enlarged adjacent to the latch tab 24. After use, the condom may be removed from the penis and replaced into the container 10. The lower layer 26 of the latch tab 24 can then be hooked underneath the lip 22 to reclose the container 10. It will be appreciated that in this arrangement, it is preferred that the lid 14 is not completely removed from the base 12 when the container 10 is opened, and it may also be preferable for the adhesive that seals the lid 14 to the base 12 to retain enough tack so as to be resealable after use. The condom can then be disposed of in the container 10.

FIG. 3 shows an alternative arrangement of the container 10 in which the base 12 is formed of a generally plastic side wall 20, with a softer base end 18. The firmer plastic side wall 20 may end in a bottom rim 30 that extends part way into the base end 18. The rim 30 may have a width of approximately ⅛" or less. The firmer side wall 20 and base rim 30 are rigid enough to allow the container 10 to be used in a dispenser, and to hold its shape during storage and transportation. The softer base end 18 can be formed of an expandable material, or a folded or crinkled material that can allow for a great degree of expansion, and may be a plastic, rubber, latex or nylon material. The container 10 with this configuration can be used as a condom applicator that can expand further along the shaft of the penis than is allowed with a non-expandable base end 18. This can allow the container 10 to be used to completely apply the condom to the penis without needing to touch the condom with their hands.

Figure 4:
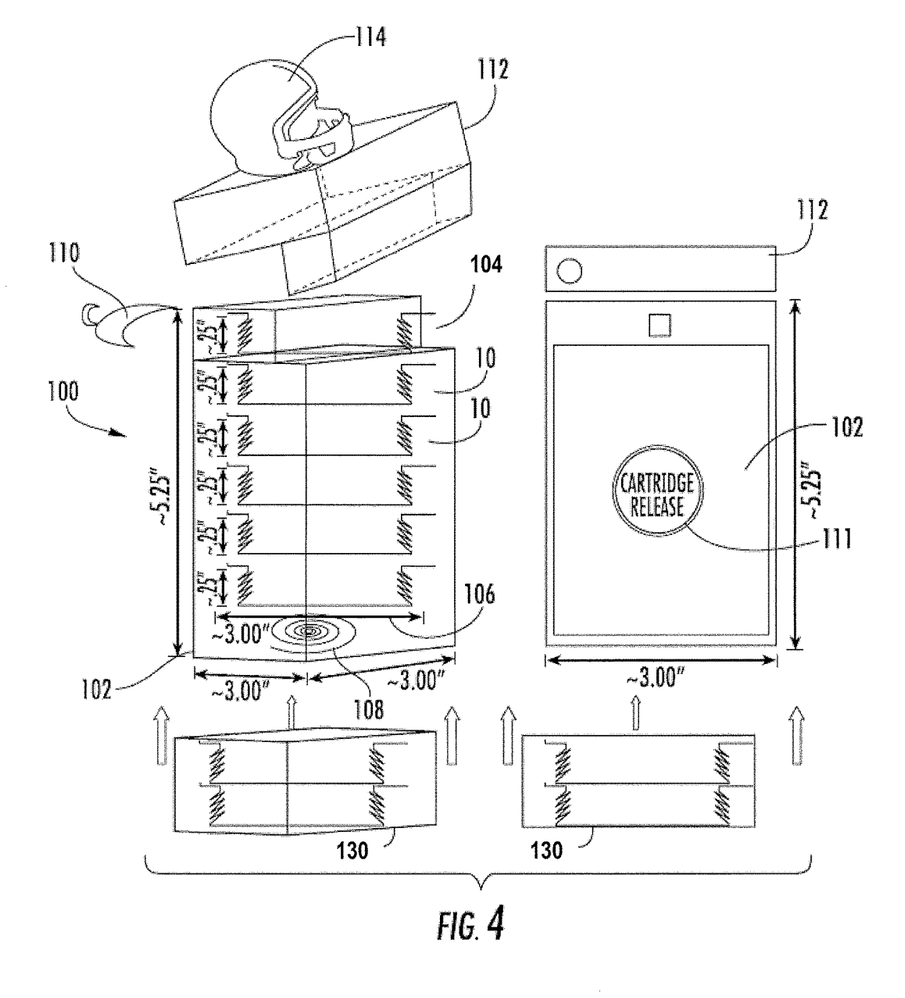
FIG. 4 shows a plurality of containers in a cartridge.

FIG. 4 illustrates an example dispenser 100 that can hold a number of containers 10, and which can be placed, for example, on a dresser or nightstand. The illustrated dispenser 100 includes a cartridge 102 that has an open top 104, and an inner movable bottom platform 106 that is spring-biased upwardly with a spring 108. A movable arm 110 can be provided at the top 104 of the cartridge 102, to hold the containers 10 in the cartridge 102 against the force of the spring 108. A removable lid 112 may also be provided. The lid 112 may alternatively be hingedly attached to the cartridge 102. As illustrated, the cartridge 102 may have a generally square cross-section, and the top 104 of the cartridge may have a stepped shape so that one half of the topmost container 10 may easily be grasped by the user for removal of the container 10 from the cartridge 100. The lid 112 may have a complementary stepped shape to the shape of the top 104 of the cartridge 102.

The movable arm 110 may be spring-biased away from the side of the cartridge 102 such that on removal of the lid 112, the arm 110 acts to aid in ejection of the topmost container 10 from the cartridge 102. The arm 110 can be arranged to push the container 10 forward by approximately 0.3875". In some arrangements, the arm 110 can be operated by a cartridge release actuator button 111. When the dispenser 100 is closed by replacement of the lid 112 after removal of the topmost container 10, the arm 108 retracts, which allows the spring-biased platform 106 to push the remaining containers 10 upwardly. The dispenser can be easily refilled through the open top 104 by moving the arm 110 and pushing containers 10 against the force of the spring 108.

Figure 7:
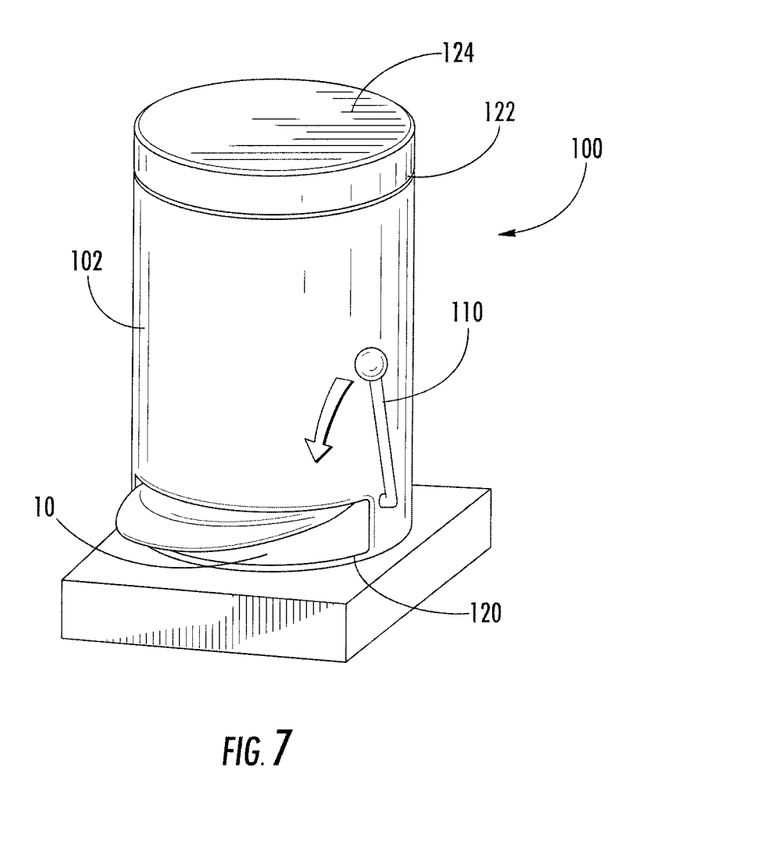
FIG. 7 is a perspective view of another arrangement of a cylindrical dispenser for storing multiple containers.

In an alternative arrangement shown in FIG. 7, the movable arm 110 can be provided at the bottom of the cartridge 102, and the dispenser 100 can have an opening 120 at the bottom of the side of the cartridge 102. The top 104 of the cartridge 102 has an opening 122 for restocking the container 100, which may be provided with a lid 124. The containers can fall to the bottom of the cartridge due to gravity, and the arm 110 can be spring-biased away from the side of the cartridge 102 to push the container 10 forward such that it projects slightly from the opening in the cartridge and can be removed. This arrangement can have a lever or other suitable mechanism to hold the movable arm 110 out of the way to allow a second container 10 to drop into place after removal of the bottom-most container 10.

It will be appreciated that other suitable arrangements of the cartridge are available for dispensing the containers 10.

In some arrangements, the cartridge 102 may have a generally cylindrical shape, or may have a generally square cross-section, such as generally cube-shaped. In some arrangements, the height of the cartridge 102 can be approximately 5.25", and the diameter of the cartridge can be approximately 3". This allows for 6 containers 10 to be stored within the cartridge. Of course, various sizes of containers 10 and dispensers 100 may be provided without departing from the scope of the invention.

A detachable "to-go" dispenser 130 may be attachable to the bottom or top of the dispenser 100, or may be provided separately. The dispenser 130 can be sized to hold 2 or 3 containers 10, and can be detached from the main dispenser 100 and carried in a user's pocket or bag. The detachable dispenser 130 can be in the form of a simple box or can, and may be a snap-fit into a bottom edge of the main dispenser 100, or may be attachable thereto by any other method known to those of skill in the art. The detachable dispenser 130 may be formed of the same material as the dispenser 100, or may be formed of a different material. For example, the dispenser 100 and detachable dispenser 130 may be formed of metal, or a rigid plastic.

The lid 112 may be provided with a removable ornament 114. The ornament 114 can be, for example, a model football helmet that can be customized to suit the user's team preferences. Any suitable ornament 114 can be used, such as a plain sphere or handle, cartoon characters, etc., and can be changed easily for decorative or promotional reasons. The ornament 114 can be attached to the lid 112 by any suitable means. For example, a magnetic disk (not shown) can be attached to the lid 112, and a suitable matching metallic disk can be provided in the ornament 114. Alternatively, the ornament 114 can be glued or screwed onto the lid 112.

Figure 5:
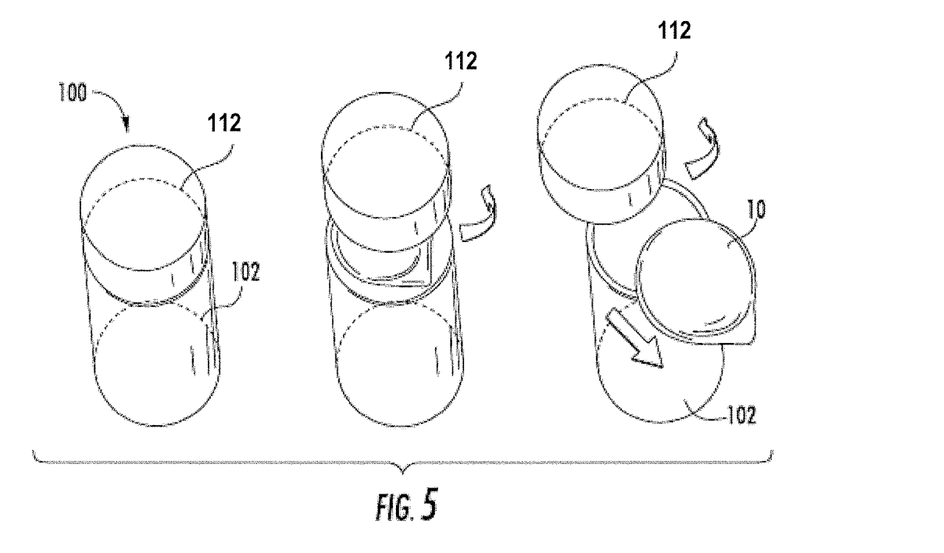
FIG. 5 is a perspective view of a cylindrical dispenser storing multiple containers.
Figure 6:
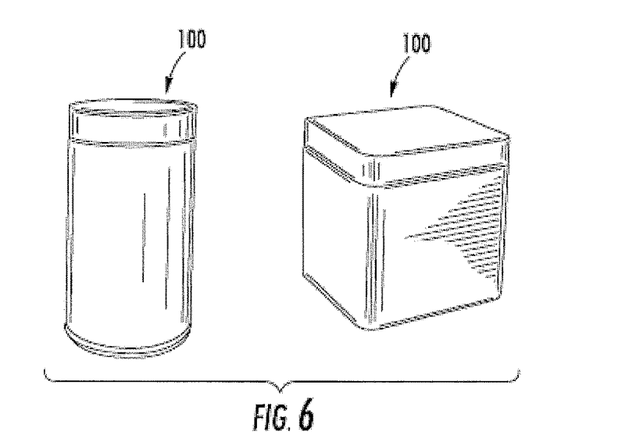
FIG. 6 shows examples of cylindrical and cubical dispensers for storing multiple containers.

FIGS. 5 and 6 show different arrangements of the dispenser 100. FIG. 5 shows an arrangement with a lid 112 that is swivel mounted to the cartridge 102. FIG. 6 shows arrangements having a sleeve or wrap thereon that includes the brand and product information, or which can be customized for promotional purposes.

Further modifications and alternative arrangements of various aspects of the invention can be apparent to those skilled in the art in view of this description. Accordingly, this description is to be construed as illustrative only and is for the purpose of teaching those skilled in the art the general manner of carrying out the invention.

It is to be understood that the forms of the invention shown and described herein are to be taken as the presently preferred arrangements. Elements and materials may be substituted for those illustrated and described herein, parts and processes may be reversed, and certain features of the invention may be utilized independently, all as would be apparent to one skilled in the art after having the benefit of this description of the invention. Changes may be made in the elements and compositions described herein or in the features or in the sequence of features of the methods described herein without departing from the spirit and scope of the invention as described in the following claim(s).

The invention claimed is:

1. A condom package comprising:
    a combined container and applicator having a generally circular cross section and including a longitudinally expandable side wall, an expandable closed end wall formed of an expandable material, and an open end including a lip, the longitudinally expandable side wall being firmer than the expandable closed end wall;
    a peel away lid attached to the open end thereof; and
    a condom provided in the container/applicator and separate from the container/applicator such that the condom is configured to be directly applied to the penis by extending the penis through the open end and into the container/applicator while the condom is still in the container/applicator and is rolled onto the penis by movement of the open end of the container/applicator down the shaft of the penis, thereby increasing a height and interior volume of the container/applicator by longitudinally expanding the longitudinally expandable side wall and expanding the expandable closed end wall resulting in an increase in an area within the container/applicator along the expandable closed end wall and unrolling the condom, the container/applicator then being removable from the condom.

2. The condom package according to claim 1, wherein the longitudinally expandable side wall of the container/applicator includes expandable accordion-like pleats.

3. The condom package according to claim 1, wherein at least the longitudinally expandable side wall is formed of a plastic material.

4. The condom package according to claim 1, comprising a lip at the open end of the container/applicator, the lip being graspable by the user to expand the side wall.

5. The condom package according to claim 1, wherein the peel away lid is resealable after use.

6. The condom package according to claim 1, wherein the peel away lid includes a rigid tab that can be grasped by the user to peel the lid from the open end of the container/applicator.

7. The condom package according to claim 6, wherein the rigid tab includes a latch that can be used to reclose the peel away lid after use.

8. The condom package according to claim 7, wherein the latch includes an upper layer and a lower layer of rigid material such that the latch is wrappable around an outer edge of a lip on the open end of the container/applicator to position the upper layer above the lip along an upper surface thereof and the lower layer underneath the lip along a lower surface thereof to hook the lip between the upper layer and lower layer of the latch to reclose the peel away lid after use.

9. A condom dispenser comprising:
    a dispenser body;
    at least two condom packages removably provided in the dispenser body including:
    a container/applicator having a longitudinally expandable side wall, a closed end wall and an open end, the container/applicator having a generally circular cross section; and
    a peel away lid attached to the open end of the container/applicator, wherein the peel away lid includes a rigid tab that is configured to be grasped by the user to peel the lid from the open end of the container/applicator, wherein the rigid tab includes a latch comprising an upper layer and a lower layer of rigid material such that the latch is wrappable around an outer edge of a lip on the open end of the container/applicator to position the upper layer above the lip along an upper surface thereof and the lower layer underneath the lip along a lower, underside, surface thereof to hook the lip between the upper layer and lower layer of the latch to reclose the peel away lid after use;
    a condom provided within an interior volume of each container/applicator and separate from the container/applicator such that the condom is configured to be directly applied to the penis while still in the container/ applicator and is rolled onto the penis by expanding a height and the interior volume of the container/applicator.

10. The condom dispenser according to claim 9, wherein the dispenser body includes a cartridge having an open end and a spring biased platform, the at least two condom packages being placed within the cartridge on the spring biased platform such that the condom packages are biased towards the open end of the dispenser body.

11. The condom dispenser according to claim 9, further comprising a removable dispenser that can be detached from the dispenser body, the removable dispenser allowing a user to carry the at least two condom packages separately from the dispenser body.

12. A condom package comprising:
a combined container and applicator having a base having an open end and an expandable interior volume having a generally circular cross-section defined by a longitudinally expandable side wall and an expandable closed end wall formed of an expandable material or a material in a folded or crinkled configuration, the longitudinally expandable side wall being firmer than the expandable closed end wall;
a flexible seal closing the open end of the base, wherein the flexible seal is formed of a flat, flexible material sealed around the side wall of the base with adhesive; and
a condom separately provided in the base of the container/applicator such that the condom is configured to be directly applied to the penis by extending the penis through the open end and into the base while the condom is still in the base after the flexible seal has been peeled at least partially back, and which is rolled onto the penis by expanding the longitudinally expandable side wall and expanding the expandable closed end wall such that an area within the base along the expandable closed end wall increases, thereby increasing a height and the interior volume of the base and unrolling the condom contained within the base as the condom is rolled onto the penis extending into the interior volume.

13. The condom package according to claim 12, wherein a rigid latch tab is provided on the flexible seal that can be hooked underneath a lip provided on the side wall of the base such that the flexible seal is recloseable to provide a receptacle for the condom after use.

14. The condom package according to claim 1, wherein the expandable closed end wall comprises material in a folded or crinkled configuration.

15. The condom package according to claim 12, wherein the expandable closed end wall comprises material in a folded or crinkled configuration.

16. The condom package according to claim 1, wherein the longitudinally expandable side wall ends in a bottom rim that extends around the expandable closed end wall.

17. The condom package according to claim 12, wherein the longitudinally expandable side wall ends in a bottom rim that extends around the expandable closed end wall.

* * * * *